(12) United States Patent
Denker et al.

(10) Patent No.: US 7,749,265 B2
(45) Date of Patent: Jul. 6, 2010

(54) RADIO FREQUENCY ANTENNA FOR A WIRELESS INTRAVASCULAR MEDICAL DEVICE

(75) Inventors: Stephen Denker, Mequon, WI (US); Cherik Bulkes, Sussex, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 1290 days.

(21) Appl. No.: 11/243,790

(22) Filed: Oct. 5, 2005

(65) Prior Publication Data

US 2007/0075905 A1 Apr. 5, 2007

(51) Int. Cl.
*A61F 2/06* (2006.01)
(52) U.S. Cl. ............. 623/1.44; 623/1.15; 623/1.21; 623/1.39; 343/718
(58) Field of Classification Search ............ 343/718; 607/88, 92, 33, 137, 32, 37, 126; 623/1.15, 623/1.21, 1.39, 1.44, 1.53
See application file for complete search history.

(56) References Cited

U.S. PATENT DOCUMENTS

| 5,358,514 | A | * | 10/1994 | Schulman et al. ........... 607/61 |
| 5,466,247 | A | * | 11/1995 | Scheiner et al. ............ 607/48 |
| 5,609,622 | A | * | 3/1997 | Soukup et al. ............ 607/122 |
| 5,611,347 | A | * | 3/1997 | Davidson ............... 600/510 |
| 5,713,939 | A | | 2/1998 | Nedungadi et al. |
| 5,713,945 | A | * | 2/1998 | Fischer et al. ............ 607/122 |
| 5,715,837 | A | * | 2/1998 | Chen ................... 128/899 |
| 5,739,795 | A | | 4/1998 | Chanteau et al. |
| 5,741,316 | A | | 4/1998 | Chen et al. |
| 5,800,500 | A | * | 9/1998 | Spelman et al. ........... 607/137 |
| 5,814,089 | A | | 9/1998 | Stokes et al. |
| 5,861,019 | A | * | 1/1999 | Sun et al. ............... 607/60 |
| 5,921,244 | A | * | 7/1999 | Chen et al. ............... 128/897 |
| 5,980,566 | A | * | 11/1999 | Alt et al. ................ 623/23.7 |
| 5,995,874 | A | | 11/1999 | Borza |
| 6,026,818 | A | | 2/2000 | Blair et al. |
| 6,053,873 | A | * | 4/2000 | Govari et al. ............ 600/505 |
| 6,067,474 | A | | 5/2000 | Schulman et al. |
| 6,138,681 | A | | 10/2000 | Chen et al. |
| 6,141,588 | A | | 10/2000 | Cox et al. |
| 6,273,904 | B1 | * | 8/2001 | Chen et al. ............... 607/88 |

(Continued)

FOREIGN PATENT DOCUMENTS

WO    WO 99/26530    6/1999

(Continued)

*Primary Examiner*—Douglas W Owens
*Assistant Examiner*—Chuc D Tran
(74) *Attorney, Agent, or Firm*—Quarles & Brady LLP; George E. Haas

(57) ABSTRACT

A radio frequency antenna is provided for use with a medical device for implantation into an animal. The antenna comprises a coil formed by a wire that includes a core formed of a shape-memory material with an electrically conductive first layer applied to an outer surface of the core. A second layer, of an electrically insulating and biologically compatible material, extends around the first layer. If necessary to reduce friction a lubricant is place between the first and second layers. If second layer is formed of porous material or a non-biological compatible material, a biological compatible outer layer surrounds the second layer thereby providing a barrier that is impermeable to body fluids of the animal.

19 Claims, 2 Drawing Sheets

U.S. PATENT DOCUMENTS

| | | |
|---|---|---|
| 6,431,175 B1 | 8/2002 | Penner et al. |
| 6,442,413 B1 | 8/2002 | Silver |
| 6,445,953 B1 * | 9/2002 | Bulkes et al. .................. 607/33 |
| 6,505,072 B1 | 1/2003 | Linder et al. |
| 6,515,346 B1 | 2/2003 | Memeny |
| 6,628,980 B2 * | 9/2003 | Atalar et al. ................. 600/423 |
| 6,746,478 B2 * | 6/2004 | Jayaraman ................. 623/1.15 |
| 6,993,394 B2 * | 1/2006 | Eggers et al. ............... 607/103 |
| 7,181,261 B2 * | 2/2007 | Silver et al. ................. 600/345 |
| 7,279,664 B2 * | 10/2007 | Weber ........................ 219/635 |
| 7,285,087 B2 * | 10/2007 | Moaddeb et al. .............. 600/37 |
| 7,481,771 B2 * | 1/2009 | Fonseca et al. .............. 600/486 |
| 7,529,589 B2 * | 5/2009 | Williams et al. ............ 607/119 |
| 2002/0005719 A1 | 1/2002 | Gilboa et al. |
| 2002/0128546 A1 | 9/2002 | Silver |
| 2003/0004568 A1 * | 1/2003 | Ken et al. .................. 623/1.46 |
| 2004/0260384 A1 * | 12/2004 | Allen ........................ 623/1.12 |
| 2005/0088357 A1 | 4/2005 | Hess et al. |

FOREIGN PATENT DOCUMENTS

WO      WO 01/63001      8/2001

* cited by examiner

RADIO FREQUENCY ANTENNA FOR A WIRELESS INTRAVASCULAR MEDICAL DEVICE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to implantable medical devices that are operated by a radio frequency signal which is received by the device, and more particularly to biologically compatible antennas for such devices.

2. Description of the Related Art

A remedy for people with slowed or disrupted natural heart activity is to implant a cardiac pacing device which is a small electronic apparatus that stimulates the heart to beat at regular rates.

Typically the pacing device is implanted in the patient's chest and has sensor electrodes that detect electrical impulses associated with in the heart contractions. These sensed impulses are analyzed to determine when abnormal cardiac activity occurs, in which event a pulse generator is triggered to produce electrical pulses. Wires carry these pulses to electrodes placed adjacent specific cardiac muscles, which when electrically stimulated contract the heart chambers. It is important that the electrodes be properly located to produce contraction of the heart chambers.

Modern cardiac pacing devices vary the stimulation to adapt the heart rate to the patient's level of activity, thereby mimicking the heart's natural activity. The pulse generator modifies that rate by tracking the activity of the sinus node of the heart or by responding to other sensor signals that indicate body motion or respiration rate.

U.S. Pat. No. 6,445,953 describes a cardiac pacemaker that has a pacing device, which can be located outside the patient, to detect abnormal electrical cardiac activity. In that event, the pacing device emits a radio frequency signal, that is received by a stimulator implanted in a vein or artery of the patient's heart. Specifically, the radio frequency signal induces a voltage pulse in an antenna on the stimulator and that pulse is applied across a pair of electrodes, thereby stimulating adjacent muscles and contracting the heart.

The stimulator in that wireless system is powered by the energy of the received signal thus requiring that the pacing device transmit a relatively strong radio frequency signal in order to provide adequate energy to the stimulator implanted deep in the patient's chest. It is desirable to place the stimulator, or at least the antenna for the stimulator, in a blood vessel located closer to the skin of the patient with electrodes implanted in one or more cardiac blood vessels and connected to the stimulator by wires extending through the electronic circuit circulatory system. This would enable more of the energy from the frequency signal to reach the stimulator, however, the blood vessels close to the skin are not sufficiently large to accommodate the size of the stimulator.

The antenna, usually in the form of a coil must possess several characteristics in order to function within the blood vessel. The coil must retain its shape in order to remain tuned to the particular radio frequency being used. The conductors of the antenna have to be insulated so that the blood and other substances flowing through the vascular system do not provide a short circuit or otherwise detune the antenna. In addition, the antenna must be biologically compatible with the blood vessel walls and with the blood.

SUMMARY OF THE INVENTION

A radio frequency antenna is provided for use with a medical device for implantation into an animal. The antenna comprises a coil formed by a wire that includes a core formed of a shape-memory material. Shape memory materials have the ability to change their size and shape in response to a particular external stimulus. For example, the shape-memory material may comprise certain metal alloys, polymers or ceramics, which respond to temperature changes or other stimuli. A first layer of electrically conductive material is applied to an outer surface of the core. A second layer extends around the first layer and is formed of an electrically insulating and biologically compatible material. For example, the second layer can be formed of expanded polytetrafluoroethylene.

In one embodiment, the second layer is bonded to the first layer. When the second layer is not bonded to the first layer, wherein movement may occur there between, a lubricant may be placed between the first and second layers. The lubricant allows expansion and contraction of the coil to occur substantially unaffected by friction between the first and second layers.

When the second layer is formed of porous material or a non-biologically compatible material, a biologically compatible outer layer extends around the second layer providing a barrier that is impermeable to body fluids of the animal.

DETAILED DESCRIPTION OF THE INVENTION

Figure 1:
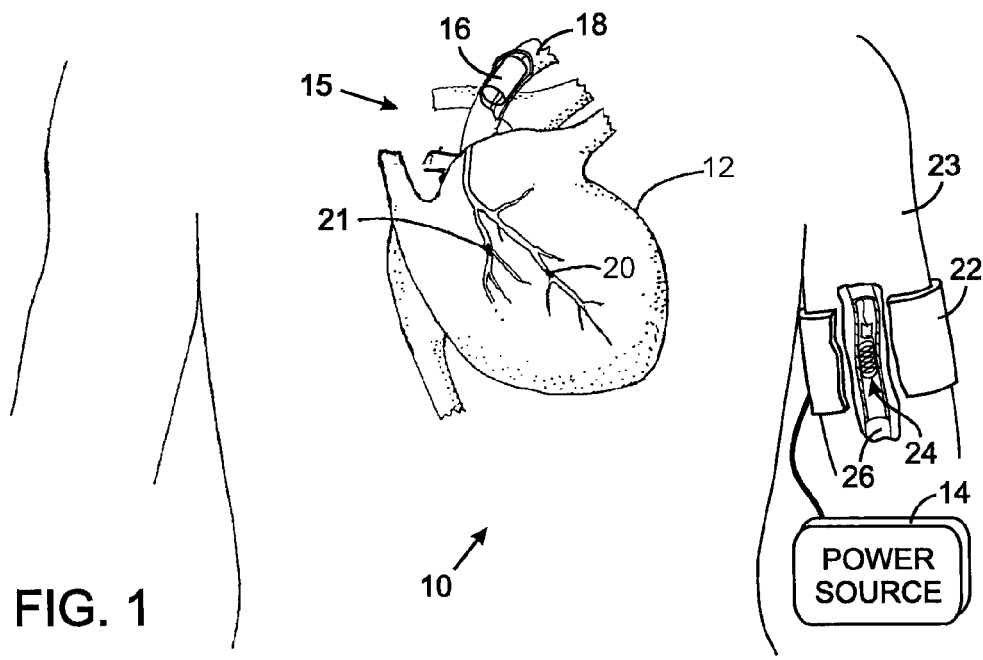
FIG. 1 is a representation of a cardiac pacing system attached to a medical patient.

With initial reference to FIG. 1, a cardiac pacing system 10 for electrically stimulating a heart 12 to contract comprises an external power source 14 and a stimulation apparatus 15 implanted in the circulatory system of a human medical patient. The stimulation apparatus 15 receives a radio frequency (RF) signal from the power source 14 worn outside the patient and the implanted electrical circuitry is electrically powered from the energy of that signal. Although the present invention is being described in the context of a cardiac pacing system 10, it has application to medical devices for stimulating other parts of a patient's body.

The power source 14 may be the same type as described in U.S. Pat. Nos. 6,445,953 and 6,907,285 and includes a radio frequency transmitter that is powered by a battery. The transmitter periodically emits a signal at a predefined radio frequency that is applied to a transmitter antenna in the form of a coil of wire within a band 22 that is placed around the patient's upper arm 23. Alternatively, another limb or area of the body, such as the neck, with an adequately sized blood vessel close to the skin surface of the human medical patient can be used. In a basic version of the cardiac pacing system 10, the radio frequency signal merely is used to convey energy for powering the stimulation apparatus 15 implanted in the patient. In a more sophisticated version of the cardiac pacing system 10, the transmitter modulates the radio frequency signal with commands received from optional circuits that configure or control the operation of the stimulation apparatus 15.

Figure 2:
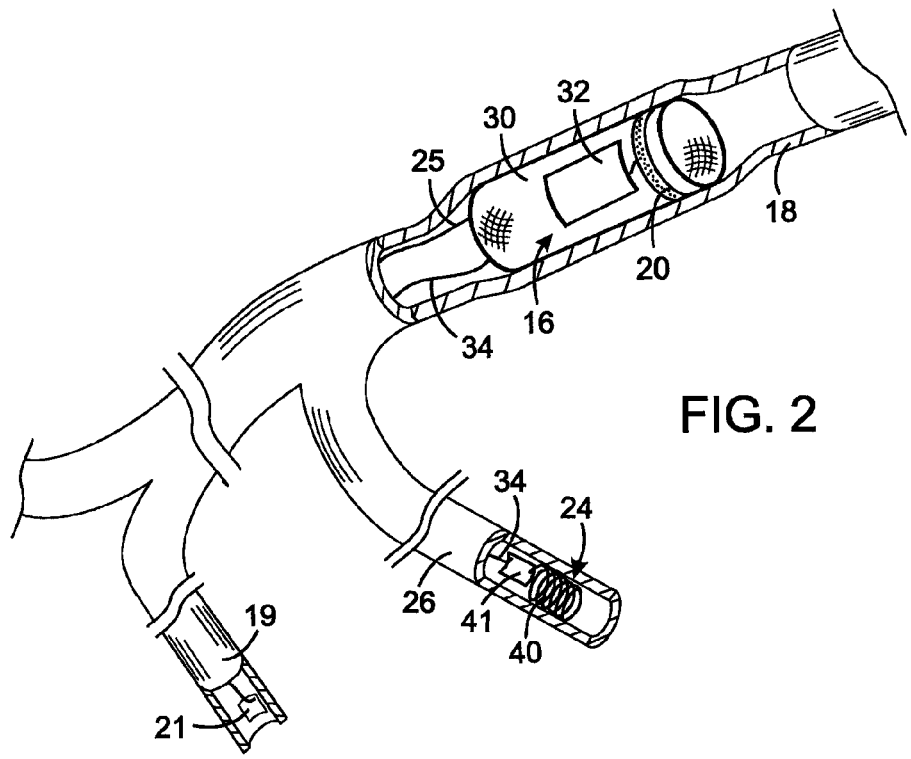
FIG. 2 is an isometric cut-away view of the patient's blood vessels in which an receiver antenna, a stimulator and a electrode have been implanted at different locations.

Referring to FIGS. 1 and 2, the implanted stimulation apparatus 15 includes an intravascular stimulator 16 located a vein or artery 18 in close proximity to the heart. Because of its electrical circuitry, the stimulator 16 is relatively large requiring a blood vessel that is larger than the arm vein, e.g. the basilic vein that is approximately five millimeters in diameter. As a result, the stimulator 16 may be embedded in the superior or inferior vena cava. Electrical wires lead from the stimulator 16 through the cardiac vascular system to one or more locations in smaller blood vessels, e.g. the coronary sinus vein, at which stimulation of the heart is desired. At such locations, the electrical wires are connected to electrodes 20 and 21 secured to the blood vessel walls.

Because the stimulator 16 of the stimulation apparatus 15 is near the heart and relatively deep in the chest of the human medical patient, a receiver antenna 24 is implanted in a vein or artery 26 of the patient's upper right arm 23 at a location surrounded by the transmitter antenna within the arm band 22. That arm vein or artery 26 is significantly closer to the skin and thus receiver antenna 24 picks up a greater amount of the energy of the radio frequency signal emitted by the power source 14, than if the receiver antenna was located on the stimulator 16.

As illustrated in FIG. 2, the intravascular stimulator 16 has a body 30 similar to well-known expandable vascular stents that are employed to enlarge a restricted vein or artery. Such vascular stents have a generally tubular design that initially is collapsed to a relatively small diameter enabling them to pass freely through a blood vessel of a patient. The stimulator body 30 and the other components of the stimulation apparatus 15 are implanted in the patient's circulatory system using a catheter and techniques similar to those employed to implant vascular stents. In an additional embodiment, the stimulator 16 is encapsulated in a biocompatible waterproof capsule floating in the bloodstream of the vessel which has significantly larger diameter. From the capsule multiple micro-coaxial cables are connected to a plurality of bipolar electrodes in small cardiac blood vessels.

The body 30 has a stimulation circuit 32 mounted thereon and, depending upon its proximity to the heart 12, may hold the first electrode 20 in the form of a ring that encircles the body. Alternatively, when the stimulator is relatively remote from the heart 12 the first electrode 20 can be remotely located in a small cardiac blood vessel much the same as the second electrode 21 (FIG. 1). The stimulation circuit 32, which may be the same type as described in the aforementioned U.S. patents, includes a power supply to which a micro-coaxial cable 34 from the receiver antenna 24 is connected. The power supply utilizes electricity from that antenna to charge a storage capacitor that provides electrical power to the stimulation circuit components. A conventional control circuit within the stimulation circuit 32 detects the electrical activity of the heart and determines when electrical pulses need to be applied to cause cardiac contractions a proper rate. When such stimulation is desired, the stimulation circuit 32 applies electrical voltage from its internal storage capacitor across the electrodes 20 and 21.

Figure 3:
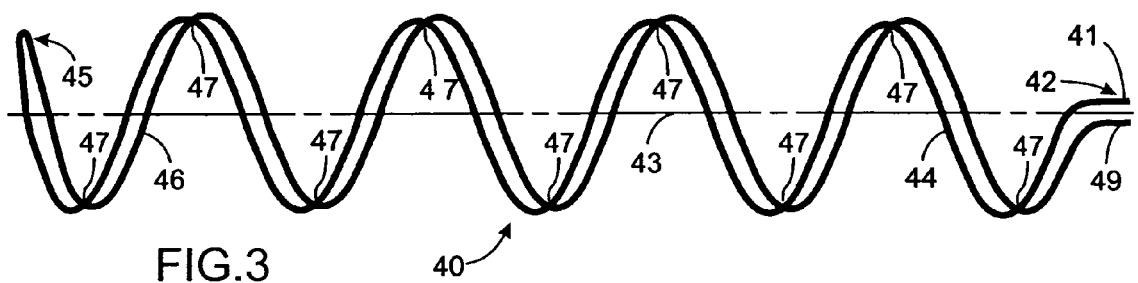
FIG. 3 depicts the receiver antenna in a configuration during implantation.

The stimulation apparatus 15 utilizes a unique receiver antenna 24 connected to the inputs of a rectifier detector 35 which converts the radio frequency signal received from the power source 14 into a DC voltage that is fed via cable 34 to the stimulation circuit 32. With reference to FIG. 3, the receiver antenna 24 comprises a coil 40 formed by an electrical conductor wound in a double helix. The coil 40 has a first terminus 41 at a first end 42 and a first helical winding 44 is wound in one rotational direction (e.g. clockwise) from that first terminus along a longitudinal axis 43 to an opposite second end 45 of the antenna coil. At the second end 45, the conductor loops into a second helical winding 46 that is wound in the same rotational direction going from the second end 45 back to the first end 42 where the second helical winding ends at a second terminus 49. Thus, the conductor of the coil 40 is wound in the same direction when forming the double helix. However, viewed from either end of the coil 40, the first helical winding 44 extends from that end in one rotational direction and the second helical winding 46 extends from that same end in the opposite rotational direction so that convolutions of the helical windings cross each other. In the embodiment illustrated in FIG. 3, the first and second helical windings 44 and 46 have the same number of turns which results in every convolution of each helical winding crossing the other helical winding at two locations 47. Although the size of the coil 40 and the number of turns may differ depending upon the particular application in which the antenna is being utilized, one application for an implantable pacing device employs a coil 40 that has a diameter of five to six millimeters, a length of two inches when deployed, and twelve turns in each helical winding 44 and 46.

The wire used to wind the double helical coil 40 has a cross section that is selected to provide the desired spring coefficient. A coil made from circular wire has a uniform spring coefficient, whereas a ribbon (wire with a rectangular cross section) or an oval wire exhibits different resistances to axial versus radial deformation. Various other cross sectional shapes can be used.

Figure 5:
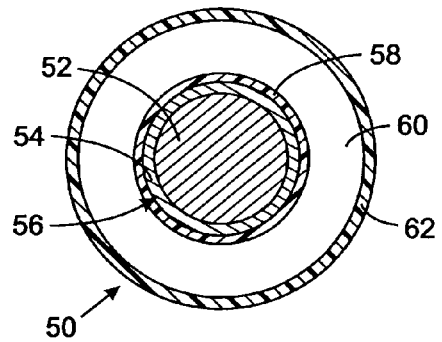
FIG. 5 is a cross section through the wire of the antenna.

FIG. 5 illustrates a example of a wire 50 with a core 52 that has a circular cross-section and which is formed of a resilient material that provides a finished antenna coil with a shape memory. As will be described, in order to insert the antenna 24 through the vasculature of a patient, the antenna coil is stretched into an elongated, smaller diameter temporary form. Upon being positioned at the desired location within the patient, the antenna coil is stimulated to contract longitudinally and expand diametrically to engage the walls of the blood vessel or other tissue of the patient. Shape memory materials have the ability to change their size and shape in response to a particular external stimulus, such as temperature, moisture, pH, or electric and magnetic fields. These materials "memorize" a permanent shape and size and can stretched or scrunched into temporary forms. Upon being exposed to the particular external stimulus, the material automatically transforms from the temporary form into the permanent size and shape. For example, nickel-titanium alloys are well known for exhibiting this shape-memory effect. The core 52 may be fabricated of such a metal alloy, thus being electrically conductive, or it may be made of a non-conductive shape memory material, such as certain well-known polymers and ceramics. Examples of other metal alloys are titanium-palladium-nickel, gold-cadmium, silver-cadmium, titanium-niobium-aluminum, uranium-niobium, hafnium-titanium-nickel, nickel-titanium, nickel-iron-zinc-aluminum, titanium-niobium, nickel-zirconium-titanium, copper-zinc-aluminum, iron-manganese-silicon, iron-manganese-silicon-chromium-nickel, nickel-titanium-copper, iron-platinum, iron-nickel-carbon, iron-palladium, iron-nickel-tin-cobalt, iron-zinc-copper-aluminum, copper-aluminum-iron, copper-aluminum-nickel, copper-tin, copper-zinc, indium-titanium, nickel-aluminum, manganese-copper, zirconium-copper-zinc, zirconium-aluminum-nickel-copper. Shape memory polymers (SMP) are special blends of two or more polymers. SMP varieties include polynorborene-, polyisoprene-, styrene butadiene-, and polyurethane-based materials and vinyl acetate- and polyester-based compounds. Additionally, two components with different thermal characteristics, such as oligo (∈-caprolactone)diol and crystallisable oligo(ρ-dioxanone)diol, have already been used separately in clinical applications such as drug delivery. The biodegradable multi-block copolymer features two block building segments, a hard segment and a 'switching' segment, which are linked together in linear chains. The higher-temperature shape is the plastic's 'permanent' form, which it assumes after heating. Furthermore, shape-memory alloy wire reinforced fiberglass composites and carbon fiber reinforced shape memory polymer composites can be used for the core 52.

If the core in electrically non-conductive or has a relatively low conductivity, the outer surface of the core 52 is coated with a layer of a material, such as gold, silver, copper or aluminum, which has a relatively high electrical conductivity. Because the antenna is intended to operate at radio frequencies, the outer region of the conductor 56 should be highly electrically conductive as the radio frequency signal travels in that region. Gold is preferred in situations where biological capability of this layer is important. Biologically compatible material refers to a substance that will not chemically interact with the patient's tissue and body fluids, which might result in either degradation of the material or alteration of the tissue or fluids. The core 52 and the conductive layer 54 form the conductor 56 of the antenna 24.

The conductor 56 is surrounded by a lubricant layer 58 to preserve the shape memory. The lubricant layer 58 may be polytetrafluoroethylene (PTFE), one brand of which is marketed under the trademark Teflon® by E.I. du Pont de Nemours and Company, Wilmington, Del. U.S.A. The sections of the wire 50 described thus far is then surrounded by a stretchable spacer layer 60 of a biologically compatible material, such as expanded polytetrafluoroethylene (ePTFE) and specifically material which is sold under the tradename Gore-Tex® by W. L. Gore & Associates, Inc., Newark, Del. U.S.A. However, other materials that provide a flexible, electrically insulating, biologically compatible layer may be utilized as the insulating layer 60.

The lubricant layer 58 is provided to minimize friction between the insulating layer 60 and the outer surface of the conductor 56 that would otherwise interfere with the expansion, contraction and other shape changes of the wire 50. If the insulating layer 60 is sufficiently flexible and can be bonded directly to the outer surface of the conductor 56, a lubricant layer 58 may not be required. When the insulating layer 60 is formed of a porous material, such as expanded polytetrafluoroethylene, bodily fluids can enter that layer and alter the dielectric properties of the antenna. In that case, the outer surface of the insulating layer 60 is covered by an outer layer 62 of a non-porous, electrically non-conductive material, such as polytetrafluoroethylene. The outer layer 62 has a thickness, which is sufficiently thin so as not to interfere with the resiliency of the wire 50.

Figure 6:
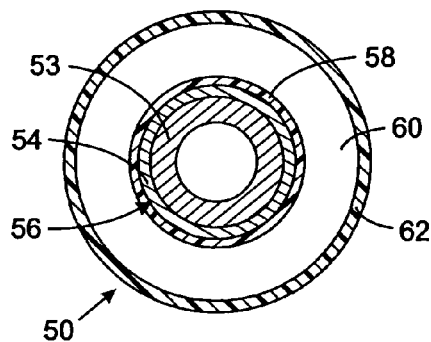
FIG. 6 is a cross section through an antenna wire with a hollow core.

FIG. 6 illustrates a similar antennas wire that has a hollow core 53 of a shape memory material.

Figure 7:
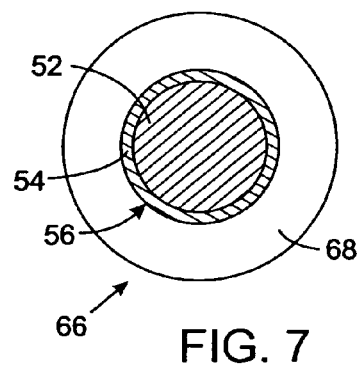
FIG. 7 is a cross section through an alternative embodiment of the antenna wire.

An alternative wire 66, shown in FIG. 7, has a single relatively thick second layer 68 of an electrical insulating material, such as polytetrafluoroethylene, utilized in place of layers 58, 60 and 62 in FIG. 5. The second layer 68 is bonded directly to the outer surface of the conductor 56.

Figure 4:
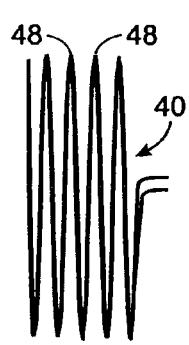
FIG. 4 illustrates the receiver antenna in a deployed configuration.

The antenna 24 is fabricated by forming the inner core 52 into the desired final shape of the antenna as depicted in FIG. 4. The shaping process utilizes the conventional technique associated with the particular type of shape-memory material utilized for the core 52. Depending upon its material, the conductive layer 54 may be applied to the core 52 prior to or after this shaping. The item then is stretched to elongate the coil after which the lubricant layer 58 is applied, such as by spraying the polytetrafluoroethylene material. Next, the fabricated sections of the stretched coil are threaded into a tubular insulator that forms the insulating layer 60. After the insulating layer 60 extends along the entire length of the coil being formed, the assembly is relaxed to return to its coil shape. The outer layer 62 is then applied, such as by spraying additional polytetrafluoroethylene thereon to complete the fabrication process.

To implant the antenna 24 in a vein or artery of a patient, the coil 40 is stretched longitudinally, which reduces its diameter, as depicted in FIG. 3. In this state, the coil is releasably attached to a catheter that is used to guide and place the antenna 24 at the desired location within the patient's vascular system. The catheter also may serve the retain the coil in the temporary shape for insertion into the patient. When the antenna has been properly located in the patient, the catheter is operated to release the coil which, due to its resiliency, contracts longitudinally which increases its diameter, thereby springing into a shape illustrated in FIG. 4.

When the coil 40 is in the deployed or contracted state the spacing between corresponding points 48 on adjacent convolutions is at least five times the width of the coil's conductor. In this expanded, or deployed, state the windings 44 and 46 are embedded into the wall of the blood vessel 26, as seen in FIG. 2, thereby securing the antenna 24 at that location.

The foregoing description was primarily directed to preferred embodiments of the invention. Even though some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

The invention claimed is:

1. A radio frequency antenna for a medical device that is implanted into an animal, said radio frequency antenna comprising:
    a coil formed by a wire wherein that wire comprises:
    (a) a core formed of a shape-memory material and having an outer surface;
    (b) a first layer of electrically conductive material applied to the outer surface of the core; and
    (c) a second layer extending around the first layer and formed of an electrically insulating and biologically compatible material; a lubricant between the first layer and the second layer.

2. The radio frequency antenna as recited in claim 1 wherein the shape-memory material is a metal alloy.

3. The radio frequency antenna as recited in claim 1 wherein the shape-memory material is an alloy selected from the group consisting of nickel-titanium, titanium-palladium-nickel, gold-cadmium, silver-cadmium, titanium-niobiumaluminum, uranium-niobium, hafnium-titanium-nickel, nickel-titanium, nickel-iron-zinc-aluminum, titanium-niobium, nickel-zirconium-titanium, copper-zinc-aluminum, iron-manganese-silicon, iron-manganese-silicon-chromium-nickel, nickel-titanium-copper, iron-platinum, iron-nickel-carbon, iron-palladium, iron-nickel-tin-cobalt, iron-zinc-copper-aluminum, copper-tin, copper-zinc, copper-aluminum-iron, copper-aluminum-nickel, indium-titanium, nickel-aluminum, manganese-copper, zirconium-copper-zinc, zirconium-aluminum-nickel-copper.

4. The radio frequency antenna as recited in claim 1 wherein the shape-memory material comprises a polymer.

5. The radio frequency antenna as recited in claim 1 wherein the shape-memory material comprises a polymer selected from the group consisting of polynorborene, polyisoprene, styrene butadiene, polyurethane, vinyl acetate, polyester, and an oligo (∈-caprolactone)diol and crystallisable oligo(ρ-dioxanone)diol compound.

6. The radio frequency antenna as recited in claim 1 wherein the core is hollow.

7. The radio frequency antenna as recited in claim 1 wherein the electrically conductive material of the first layer is selected from the group consisting of silver, gold, copper, aluminum, steel, and alloys of one or more of those metals.

8. The radio frequency antenna as recited in claim 1 wherein the second layer is formed of expanded polytetrafluoroethylene.

9. The radio frequency antenna as recited in claim 1 wherein the second layer is bonded to the first layer.

10. The radio frequency antenna as recited in claim 1 further comprising an outer layer extending around the second layer and providing a barrier that is impermeable to body fluids of the animal.

11. The radio frequency antenna as recited in claim 1 wherein the first layer of electrically conductive material coats to outer surface of the core.

12. The radio frequency antenna as recited in claim 1 wherein the first layer of electrically conductive material is adapted for connection to a radio frequency circuit.

13. A radio frequency antenna for a medical device that is implanted into an animal, said radio frequency antenna comprising a coil formed by a wire that comprises:
   a core formed of a resilient material and having an outer surface;
   a first layer of electrically conductive material applied to the outer surface of the core;
   a lubricant layer extending around the first layer;
   a second layer extending around the lubricant layer and formed of an electrically insulating and biological compatible material; and
   an outer layer extending around the second layer and providing a barrier that is impermeable to body fluids of the animal.

14. The radio frequency antenna as recited in claim 13 wherein the resilient material is a shape-memory metal alloy.

15. The radio frequency antenna as recited in claim 14 wherein the shape-memory material selected from the group consisting of a polymer and a ceramic.

16. The radio frequency antenna as recited in claim 13 wherein the electrically conductive material of the first layer is selected from the group consisting of silver, gold, copper, aluminum, and alloys of one or more of those metals.

17. The radio frequency antenna as recited in claim 13 wherein the lubricant layer is formed of polytetrafluoroethylene.

18. The radio frequency antenna as recited in claim 13 wherein the second layer is formed of expanded polytetrafluoroethylene.

19. The radio frequency antenna as recited in claim 13 wherein the outer layer is formed of polytetrafluoroethylene.

* * * * *